United States Patent [19]
Ulrich et al.

[11] Patent Number: 5,911,576
[45] Date of Patent: Jun. 15, 1999

[54] MEASUREMENT DEVICE FOR QUANTIFYING THE SEVERITY OF BRUXISM

[75] Inventors: Karl T. Ulrich, Narberth, Pa.; Lee Weinstein, Somerville, Mass.; K. Alex McDonald, Houston, Tex.; Clay A. Burns, New York, N.Y.

[73] Assignee: BruxCare, L.L.C., Austin, Tex.

[21] Appl. No.: 09/006,365

[22] Filed: Jan. 13, 1998

Related U.S. Application Data

[60] Provisional application No. 60/035,506, Jan. 15, 1997.

[51] Int. Cl.⁶ .................................................. A61C 19/04
[52] U.S. Cl. ............................ 433/68; 433/215; 128/848
[58] Field of Search ..................... 433/6, 68, 69, 433/215; 128/848, 859, 861; 600/590; 604/51

[56] References Cited

U.S. PATENT DOCUMENTS

| | | | |
|---|---|---|---|
| 3,421,223 | 1/1969 | Stark | 433/70 |
| 3,813,781 | 6/1974 | Forgione | 433/68 |
| 5,460,527 | 10/1995 | Kittelsen | 433/215 |
| 5,503,552 | 4/1996 | Diesso | 433/371 |
| 5,586,562 | 12/1996 | Matz | 128/848 |

*Primary Examiner*—John J. Wilson
*Attorney, Agent, or Firm*—Steven J. Weissburg

[57] ABSTRACT

A bruxism monitoring device comprising a thin shell formed to the shape of and elastically retained to one or more teeth, said shell further comprising: a plurality of layers having mutually distinguishable colors, each color distinguishable from the colors of adjacent layers; and a material thickness that is greater anteriorly than posteriorly. The outer layer of the shell, when worn away by grinding action, reveals an inner layer. The regions of wear may be analyzed to determine the extent of the bruxing activity.

37 Claims, 3 Drawing Sheets

5,911,576

MEASUREMENT DEVICE FOR QUANTIFYING THE SEVERITY OF BRUXISM

This application claims the benefit of U.S. Provisional Application No. 60/035,506, filed Jan. 15, 1997.

BACKGROUND

This invention relates to bruxism measurement devices and more particularly to an intraoral appliance for quantifying the extent of wear due to the grinding action of teeth.

Bruxism has generally been defined as the nonfunctional clenching, grinding, gritting, gnashing, and clicking of the teeth. Bruxism can occur while a person is awake or asleep. When the phenomenon occurs during sleep, it is called nocturnal bruxism. Even when it occurs during waking hours, the bruxist is often not conscious of the activity. Biting force exerted during bruxism often significantly exceeds peak biting force exerted during normal chewing. Biting forces exceeding 700 pounds have been measured during bruxing events. Chronic bruxism may result in musculoskeletal pain, headaches, and damage to the teeth and/or the temporomandibular joint.

The symptoms of bruxism include: clicking or grinding noises detected by a sleeping partner, wear facets on a bruxist's tooth surfaces, jaw pain, headaches, damage to teeth or dental work, and over development of the jaw muscles. When bruxism is severe, it may be accurately diagnosed by the presence of jaw pain and over development of the jaw muscles. When bruxism is less severe, it may be difficult to diagnose. For example, wear facets are often detected by a dentist during a dental examination, but may have resulted from bruxing during a previous period of the patient's life. Because nocturnal bruxism is a subconscious activity, bruxists may not be aware of their bruxing and may not believe that they brux even when presented with strong circumstantial evidence.

The primary treatment for nocturnal bruxism is the use of intraoral occlusal splints or "mouth guards," which are generally semi-rigid plastic covers for the upper or lower teeth. Occlusal splints are generally fabricated for a specific individual from an impression taken of the individual's teeth. While the splints protect the teeth from wear due to bruxism, research indicates that they may exacerbate or reduce the bruxism itself depending on the particularities of the situation.

Occlusal splints are relatively expensive sometimes costing a bruxist more than $500. Occlusal splints also present numerous inconveniences to the user. They require frequent cleaning, are difficult to clean, require periodic replacement, inhibit speech, and are frequently lost. For couples sleeping together, occlusal splints are far from romantic. Some users perceive that occlusal splints accelerate tooth decay. As a result of these and other perceived disadvantages, without compelling evidence of current bruxism, dentists and patients are reluctant to procure an occlusal splint.

It is the object of this invention to provide an incontrovertible, inexpensive, and convenient means for measuring the severity of bruxism.

SUMMARY

The invention consists of a bruxism measurement device including a thin shell formed to fit closely over either the upper or lower teeth. The shell is thin enough that it does not interfere substantially with the normal occlusal action of the user's teeth. It is thin enough and fits tightly enough that the device is comfortable and does not interfere with normal speech, breathing, or tongue motion.

The shell consists of one or more layers of material. In a preferred embodiment, an outer layer, nearest the occlusal interface, wears away when substantial bruxing occurs, revealing an inner layer of material. This inner layer of material is optically distinguishable from the outer layer, so that the location and severity of the bruxism can be determined.

Because the jaw muscle opens in a combination of linear and angular motions, the shell may be tapered from the front of the mouth to the rear of the mouth so that the teeth meet in a normal bite pattern when the shell is worn.

BRIEF DESCRIPTION OF THE DRAWINGS

These and other features, aspects, and advantages of the present invention will become better understood with regard to the following description, appended claims and accompanying drawings, where:

DETAILED DESCRIPTION

In use, at least one shell is formed to fit a particular patient. The patient may then wear a shell over a predetermined period. The shell may then be examined and the wear quantified.

Figure 1:
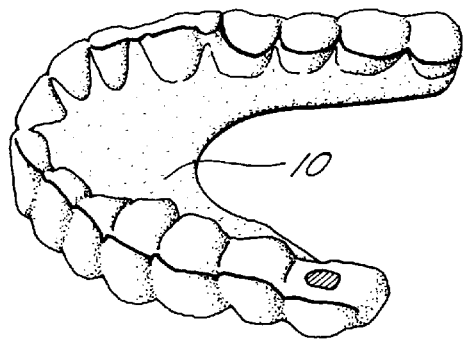
FIG. 1 is an overall perspective view of an embodiment of the invention comprising multiple layers of material.

In a preferred embodiment of the invention, the shell 10 in FIG. 1 is formed to fit the upper, or maxillary, teeth. The shell fits closely over the tooth 30 in FIG. 3, including a portion of the sides of the tooth. Because the sides of at least some teeth are narrower at the gum line than at their widest point, the shell "snaps" lightly over the teeth and is retained elastically.

The shell is preferably fabricated by forming a thin sheet of heated polymeric material over a pattern made from the patient's teeth. This forming may be accomplished by a pressure or vacuum forming machine such as the BioStar pressure forming machine manufactured by Schedu Dental.

The shell is made from a material that is easily deformed in order to snap over the teeth, but that is not so stiff that the forces exerted by the shell on the teeth cause discomfort. In a preferred embodiment the shell is formed from polyvinylchloride, with a thickness before forming of approximately 0.5 mm.

In a preferred embodiment, the shell consists of a plurality of layers, each layer distinguishable from the adjacent layers. In another preferred embodiment, each of the layers is a different color so that the regions of wear can be detected and measured optically.

The outermost layer of the shell, the one visible when the shell is engaged on the teeth, is preferably tooth colored, so that the shell is not easily noticed by observers.

Figure 2:
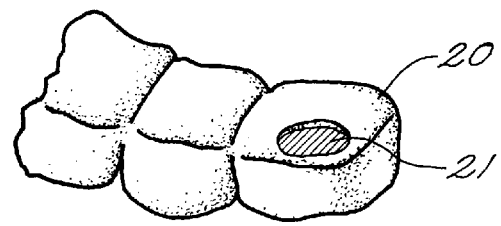
FIG. 2 is a perspective view of a portion of the shell in FIG. 1 showing a worn region revealing the inner layer of material.

In a multi-layered embodiment, when a particular region of the shell is worn away, an underlying layer is exposed. FIG. 2 shows an embodiment of the invention in which the outer layer 20 is worn away revealing an inner layer 21. When a two-layer shell is used, the extent of bruxism is indicated by the area of the worn regions. When using a shell consisting of three or more layers, the depth of wear may also be easily determined from the observed wear patterns and used to refine the measure.

Figure 3:
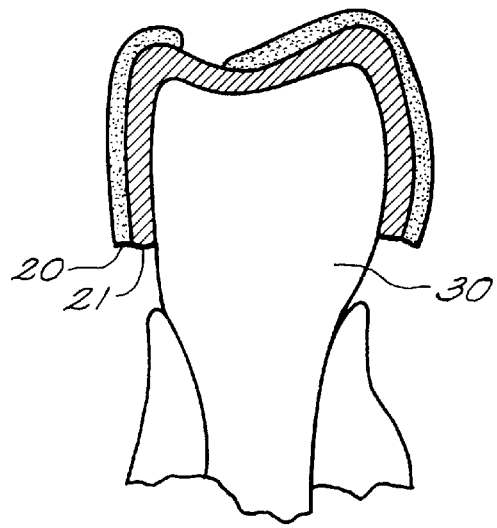
FIG. 3 is a cross-sectional view of the shell in FIGS. 1 and 2 and of a corresponding tooth.

In a preferred embodiment, the shell 10 in FIG. 3, is formed from two layers of polyvinylchloride. The outermost layer 20 is 0.075 mm thick and the innermost layer 21 is 0.425 mm thick. The outermost layer is ivory colored and the innermost layer is orange colored.

In another preferred embodiment the shell is formed from two layers. The innermost layer is 0.425 mm thick and is orange-colored polyvinylchloride. The outermost layer consists of a 0.075 mm thick layer of white ink or paint applied to the innermost layer. Other color and material combinations are possible.

In another preferred embodiment, the outer layer is non-wetting for a phosphorescent or fluorescent dye; and the inner layer is wetting for the dye. When the outer layer is worn through, an inner layer is exposed which can be wet by a dye. The regions of wear may then be distinguished optically by first dipping the shell in the dye, and then observing the fluorescence or phosphorescence in the image.

In another preferred embodiment, the outer layer is opaque to ultraviolet—UV—light, and the inner layer is made of a phosphorescent material. When exposed to UV light, the worn regions of the shell will be illuminated.

In another preferred embodiment, the shell is translucent. In this embodiment, regions of wear will transmit more light than regions of non-wear. Wear may therefore be observed by illuminating the shell from one side and observing differences in the amount of transmitted light from the other side.

The effect of a two-layer shell need not be accomplished with two distinct materials. In a preferred embodiment one "layer" may be the surface finish of the shell with the inner "layer" the underlying material. In a preferred embodiment, a shiny finish on the outer surface of the shell is worn away by the bruxing action, creating dull spots on the shell. These dull spots may be detected visually.

The optically distinguishable layers allow for electronic imaging and automated measurement of the worn regions of the shell. In a preferred embodiment, the layers of the shell are made of materials that are distinguishable by standard red-green-blue—i.e., RGB—digital imaging.

In a preferred embodiment, the outermost layer of the shell includes a dull finish to avoid reflections and the resulting bright spots in an optical image, which could be confused with worn regions of the shell when automatically analyzing a digital image.

Figure 4A:
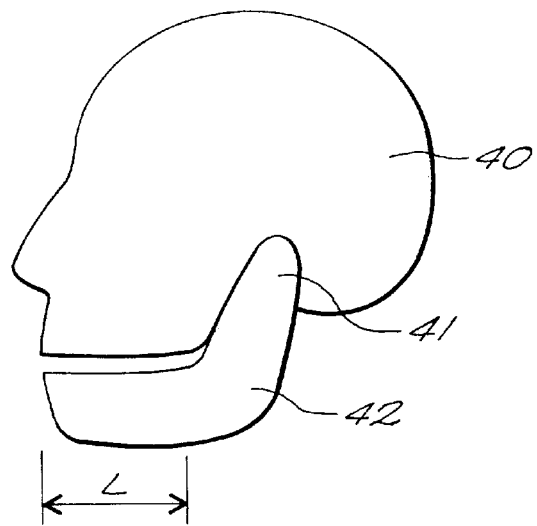
FIG. 4a is a diagram of the human jaw, tooth, and skull system in a closed position.
Figure 4B:
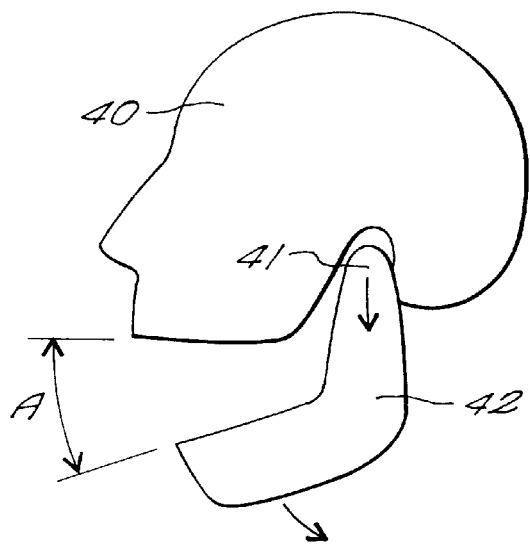
FIG. 4b is a diagram of the human jaw, tooth, and skull system in an open position.
Figure 5:
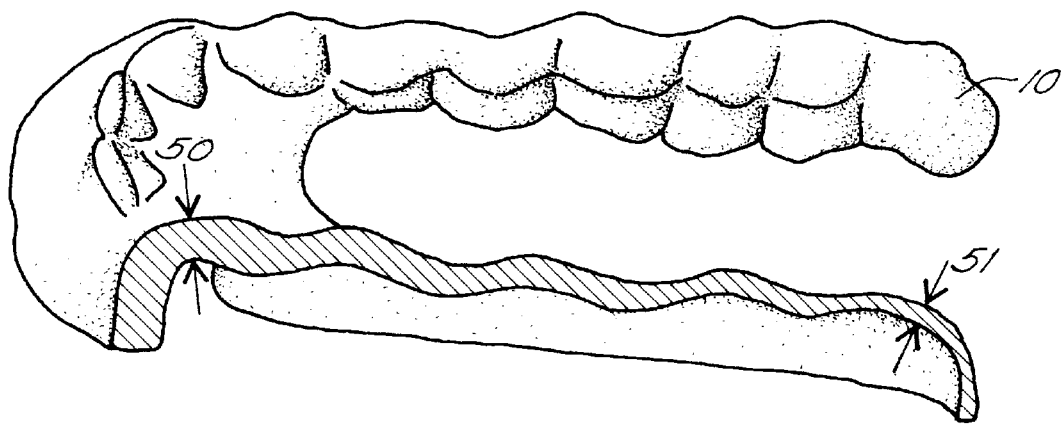
FIG. 5 is a perspective view of an embodiment of the invention showing an alphanumeric identification code.

The human jaw is a complex joint involving both linear and angular motions when opening and closing. In FIG. 4, jaw 41, skull 40, and jaw joint 41 are shown schematically. When the jaw opens, there is both vertical linear translation and angular rotation. Let L be the length from front to back of the set of occlusal surfaces of the teeth. Let A be the angle with respect to the upper teeth that the jaw assumes when open. This angle is called the Frankford Mandibular Angle. When the upper and lower teeth are in contact, the angle A is zero by definition. If the jaw opened only linearly, i.e., if A remained zero as the jaw opened, then the introduction of a shell of constant thickness between the upper and lower teeth would not disturb the normal occlusal pattern of the teeth. However, few individuals have jaws with this characteristic. Humans more frequently have a visually noticeable jaw angle, A, when the jaw is fully open. When the jaw is open to accommodate a shell thickness of approximately 0.50 mm, the value of A may be as much as 0.50 degrees. As a result, when a shell of constant thickness is introduced between the upper and lower teeth, the teeth closest to the jaw joint may make contact with the shell, while the teeth distal from the jaw joint do not make contact. In effect, the jaw is "wedged open" by the shell. In a preferred embodiment, the shell 10 in FIG. 5 is tapered from front to rear so that the thickness 50 is greater than the thickness 51. This taper allows for contact between the teeth and the shell along its entire length, and gives rise to a more natural occlusal pattern. The difference between thickness 50 and thickness 51 is approximately equal to L multiplied by the Sine of the angle A. For L equal to 50 mm, and A equal to 0.25 degrees, when the jaw is open to accommodate a shell of thickness 51, the difference between thicknesses 51 and 50 is approximately 0.22 mm. In a preferred embodiment, the taper is continuous from front to rear.

Figure 6:
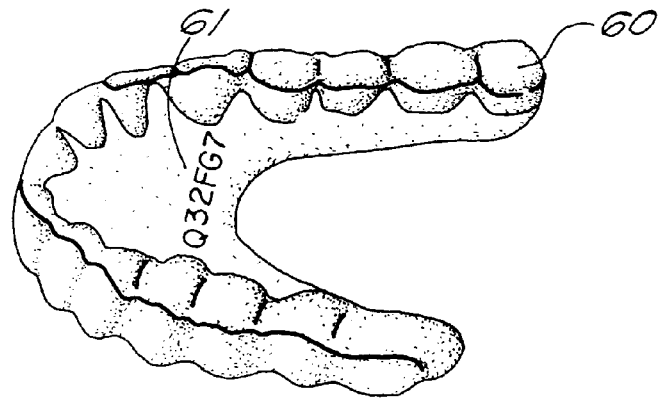
FIG. 6 is a perspective view of an embodiment of the invention showing an alphanumeric code.

Although shells are preferably formed for each particular patient, shells for different patients look alike and are difficult to distinguish from one another. Without some identification means, the only way to positively verify a match between shell and patient is to test the fit. Testing the fit requires subsequent sterilization in the event of a mismatch and is perceived by the patient to be unprofessional. Furthermore, for an agent analyzing the wear of the shell, verifying the identity of a shell by testing the fit may not be possible because the patient may not be present. To avoid these problems, the invention includes a coded identification label on the shell. In a preferred embodiment, the shell 60 in FIG. 6 includes an alphanumeric identification code 61. This code uniquely identifies the patient, the prescribing dentist, and the ordinal rank of the shell among those formed for the patient.

Figure 7:
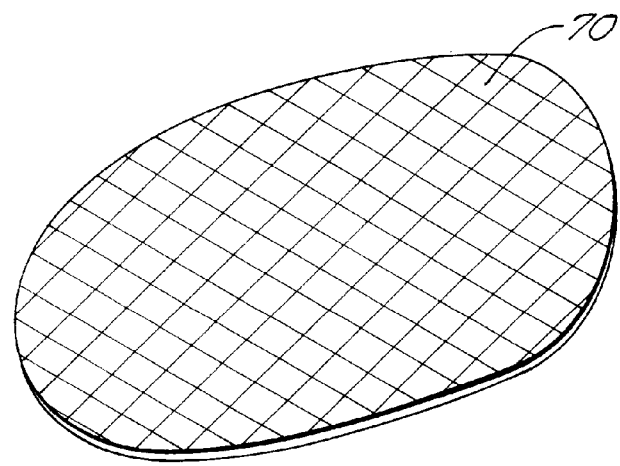
FIG. 7 is a top view of a disc of material, from which a shell may be formed, showing a grid pattern.

In a preferred embodiment, the tapered thickness of the shell is obtained by forming the shell from a flat disc that is also initially tapered. Because a thermal forming process gives rise to deformation and stretching of the material, the thickness of the shell may differ from the initial thickness of the disc from which the shell is formed. In a preferred embodiment, a grid pattern is included on one side of the disc 70 in FIG. 7. This pattern gives a visual indication of the amount of stretching that occurs during forming. If the grid remains geometrically regular after forming, the thickness of the shell is tapered proportionally to the taper of the original disc. If, in contrast, the grid is irregular, then the taper of the shell may be disproportionate to that of the original disc of material. This information may be used in at least two ways. First, if the deformation is very irregular, the shell may be rejected and another formed. Second, an estimate of the amount of stretching revealed by the grid may be used to correct the estimate of the severity of the wear. For example, an indication of wear in a more highly stretched, and therefore thinner, region of the shell is less severe than wear in a thicker region of the shell.

The human mouth contains many types of bacteria, some of which are harmful. In a preferred embodiment, the shell includes a disinfectant coating to inhibit the growth of harmful bacteria.

Over a prolonged period of use, the shell may develop an unpleasant taste and odor. In a preferred embodiment, the shell includes a mint flavor and scent. Other flavors and scents, such as cinnamon or citrus, are possible.

The foregoing discussion should be understood as illustrative and should not be considered to be limiting in any sense. While this invention has been particularly shown and described with reference to preferred embodiments thereof, it will be understood by those skilled in the art that various changes in form and details may be made therein without departing form the spirit and scope of the invention as defined by the claims.

Having described the invention, what is claimed is:

1. A bruxism monitoring device comprising:
   a. a shell formed to the shape of and elastically retainable to one or more teeth, said shell further comprising:
      i. a material thickness less than 1.25 mm;
      ii. a plurality of layers having mutually distinguishable colors, each color distinguishable from the colors of adjacent layers;
      iii. a material thickness that is greater anteriorly than posteriorly.
2. The device of claim 1 wherein at least one of said layers comprises an ink-like coating covering a majority of the outward-facing area of an adjacent layer of said shell.
3. The device of claim 1 wherein at least one of said layers is wetting for a dye and at least one of said layers is non-wetting for a dye.
4. The device of claim 1 wherein at least one of said layers is phosphorescent.
5. The device of claim 1 wherein at least one of said layers is fluorescent.
6. The device of claim 1 wherein the outermost surface of said shell comprises a dull finish.
7. The device of claim 1 wherein the anterior region of the outermost layer is tooth colored.
8. The device of claim 1 further comprising a flavoring.
9. The device of claim 1 further comprising a fragrance.
10. The device of claim 1 further comprising a disinfectant.
11. The device of claim 1 further comprising a coded label uniquely identifying said device.
12. The device of claim 11 wherein said label comprises an alphanumeric code.
13. The device of claim 1 further comprising a surface pattern to indicate the degree of material stretching resulting from the forming of said shell.
14. The device of claim 13 wherein said pattern is a grid.
15. A bruxism monitoring device comprising:
    a. a shell formed to the shape of and elastically retainable to one or more teeth, said shell further comprising:
       i. a material thickness less than 1.25 mm;
       ii. a plurality of layers having mutually distinguishable colors, each color distinguishable via standard RGB digital imagery;
       iii. a material with surface characteristics minimizing specular reflection.
16. The device of claim 15 wherein at least one of said layers comprises an ink-like coating covering a majority of the outward-facing area of an adjacent layer of said shell.
17. The device of claim 15 wherein at least one of said layers is wetting for a dye and at least one of said layers is non-wetting for a dye.
18. The device of claim 15 wherein at least one of said layers is phosphorescent.
19. The device of claim 15 wherein at least one of said layers is fluorescent.
20. The device of claim 15 wherein the anterior region of the outermost layer is tooth colored.
21. The device of claim 15 further comprising a flavoring.
22. The device of claim 15 further comprising a fragrance.
23. The device of claim 15 further comprising a disinfectant.
24. The device of claim 15 further comprising a coded label uniquely identifying said device.
25. The device of claim 24 wherein said label comprises an alphanumeric code.
26. The device of claim 15 further comprising a surface pattern to indicate the degree of material stretching resulting from the forming of said shell.
27. The device of claim 26 wherein said pattern is a grid.
28. A bruxism monitoring device comprising:
    a. a shell formed to the shape of and elastically retainable to one or more teeth, said shell further comprising:
       i. a material thickness less than 1.25 mm;
       ii. an outward-facing material surface that is shiny; said surface becoming substantially less spectral when abraded by tooth grinding.
29. The device of claim 28 wherein the anterior region of the outermost layer is tooth colored.
30. The device of claim 28 further comprising a flavoring.
31. The device of claim 28 further comprising a fragrance.
32. The device of claim 28 further comprising a disinfectant.
33. The device of claim 28 further comprising a coded label uniquely identifying said device.
34. The device of claim 33 wherein said label comprises an alphanumeric code.
35. The device of claim 28 further comprising a surface pattern to indicate the degree of material stretching resulting from the forming of said shell.
36. The device of claim 35 wherein said pattern is a grid.
37. A bruxism monitoring device comprising:
    a. a shell formed to the shape of and elastically retainable to one or more teeth, said shell further comprising:
       i. a material thickness less than 1.25 mm;
       ii. a plurality of layers having different colors, each color distinguishable via standard RGB digital imagery;
       iii. a material with surface characteristics minimizing specular reflection.
       iv. a material thickness that is greater anteriorly than posteriorly.

* * * * *